(12) United States Patent
Kim (10) Patent No.: US 12,042,575 B2
(45) Date of Patent: Jul. 23, 2024

(54) NON-CONTACT MICROPLASMA OZONIZED MIST RADICAL STERILIZER

(71) Applicant: CAST CO.,LTD., Seoul (KR)

(72) Inventor: Min Hwan Kim, Seoul (KR)

(73) Assignee: CAST CO.,LTD., Seoul (KR)

( * ) Notice: Subject to any disclaimer, the term of this patent is extended or adjusted under 35 U.S.C. 154(b) by 0 days.

(21) Appl. No.: 18/253,815

(22) PCT Filed: Oct. 29, 2021

(86) PCT No.: PCT/KR2021/015386
§ 371 (c)(1),
(2) Date: May 22, 2023

(87) PCT Pub. No.: WO2022/114556
PCT Pub. Date: Jun. 2, 2022

(65) Prior Publication Data
US 2023/0338597 A1 Oct. 26, 2023

(30) Foreign Application Priority Data
Nov. 25, 2020 (KR) .......................... 10-2020-0160096

(51) Int. Cl.
*A61L 2/00* (2006.01)
*A61L 2/20* (2006.01)
(Continued)

(52) U.S. Cl.
CPC ................ *A61L 2/202* (2013.01); *A61L 2/26* (2013.01); *A61L 9/046* (2013.01); *A61L 9/122* (2013.01);
(Continued)

(58) Field of Classification Search
CPC ........... A61L 2/24; A61L 9/14; G05D 7/0629; B05B 17/0607
(Continued)

(56) References Cited

U.S. PATENT DOCUMENTS

| 2016/0216712 A1* | 7/2016 | Baumgartner | ............ A61L 2/24 |
| 2017/0066003 A1* | 3/2017 | Baumgartner | ............ A61L 9/14 |

FOREIGN PATENT DOCUMENTS

| JP | 2003-199814 A | 7/2003 |
| JP | 2013-153897 A | 8/2013 |

(Continued)

*Primary Examiner* — Monzer R Chorbaji
(74) *Attorney, Agent, or Firm* — NKL Law; Byungwoong Park (57) ABSTRACT

The present invention relates to a non-contact microplasma ozonized mist radical sterilizer. The present invention minimizes two discharge spaces to a micro size to lower a breakdown voltage, concentrates electromagnetic fields using micro-patterns to induce micro-discharge at a normal pressure, and generates plasma through glow discharge, to increase electron density and reduce power consumption according to generation of microplasma. When oxygen and air are injected as reaction gases using this principle, ozone is generated as active species, and the generated ozone is used for various purposes such as removing pests, reducing ethylene, and sterilizing harmful bacteria. Sterilization is improved by sterilizing air and generating mist using ozone generated from microplasma, and then decomposition and drying of ozone gas are performed using a heat generation device and a catalytic method.

3 Claims, 7 Drawing Sheets

(51) Int. Cl.
  *A61L 2/26* (2006.01)
  *A61L 9/00* (2006.01)
  *A61L 9/04* (2006.01)
  *A61L 9/12* (2006.01)
  *B05B 17/04* (2006.01)
(52) U.S. Cl.
  CPC ........ *A61L 2202/11* (2013.01); *A61L 2202/13* (2013.01); *A61L 2202/15* (2013.01); *A61L 2202/16* (2013.01); *A61L 2209/212* (2013.01)
(58) Field of Classification Search
  USPC .................. 422/28, 292, 305–306; 239/4, 73
  See application file for complete search history.

(56) References Cited

FOREIGN PATENT DOCUMENTS

| KR | 10-2005-0113356 A | 12/2005 |
| KR | 10-2017-0042173 A | 4/2017 |
| KR | 10-1839823 B1 | 3/2018 |
| KR | 10-2019-0040392 A | 4/2019 |

* cited by examiner

NON-CONTACT MICROPLASMA OZONIZED MIST RADICAL STERILIZER

CROSS-REFERENCE TO RELATED APPLICATIONS

This application is a National Stage Entry of PCT/KR2021/015386, filed on Oct. 29, 2021, which claims a priority to Korean Patent Application No. 10-2020-0160096, filed Nov. 25, 2020, the entire contents of which are hereby incorporated by reference.

BACKGROUND

Technical Field

The present invention relates to a non-contact microplasma ozonized mist radical sterilizer that generates mist using ozone generated with low-temperature microplasma and performs sterilization using OH radicals generated in water.

Background Art

Plasma is defined as the fourth state of material following solid, liquid, and gas according to the magnitude of the internal energy of particles constituting a material.

Plasma generated in an ultra-high temperature state produces highly reactive chemical species in a completely dissociated or incompletely ionized molecular state without a high gas temperature.

When electrical energy is applied to an atom or molecule in a gaseous state, the nucleus, which is electrically positively charged, and the electrons distributed around the nucleus are separated, resulting in a gaseous state composed of ions and electrons. In the plasma generated at an ultra-high temperature, molecules are completely dissociated into an atomic state, and all electrons bound to the atoms are released from electron orbits as free electrons, resulting in a gaseous state composed of ions and electrons. However, if the plasma temperature is not high, completely dissociated molecules, incompletely ionized ionic molecules or ionic atoms, and the like result in highly reactive chemical species (radicals).

Meanwhile, ozone is one of active species produced by reaction of chemical species generated in a plasma state based on oxygen, and this ozone has strong sterilizing power and is reduced to oxygen after sterilization, and thus ozone is environmentally friendly.

As related prior art, there is Korean Patent No. 10-1839823, "Modular Microplasma Microchannel Reactor Device, Small Reactor Module, and Ozone Generating Device." Korea Patent No. 10-1839823 merely discloses a technique of creating a microchannel inside a non-insulator and passing gases through the microchannel to generate plasma in the channel.

SUMMARY

In order to solve the above-described problems, an object of the present invention is to provide a non-contact microplasma ozonized mist radical sterilizer that generates mist using ozone generated with low-temperature microplasma and performs sterilization using OH radicals generated in water.

Another object of the present invention is to operate a heat generating device and an ozone depletion filter to reduce ozone to oxygen in order to process residual ozone remaining after use for sterilization and to perform final sterilization by collecting mist.

Another object of the present invention is to improve sterilization by sterilizing air and generating mist using ozone generated from microplasma.

Means of Solving the Problem

Figure 1:
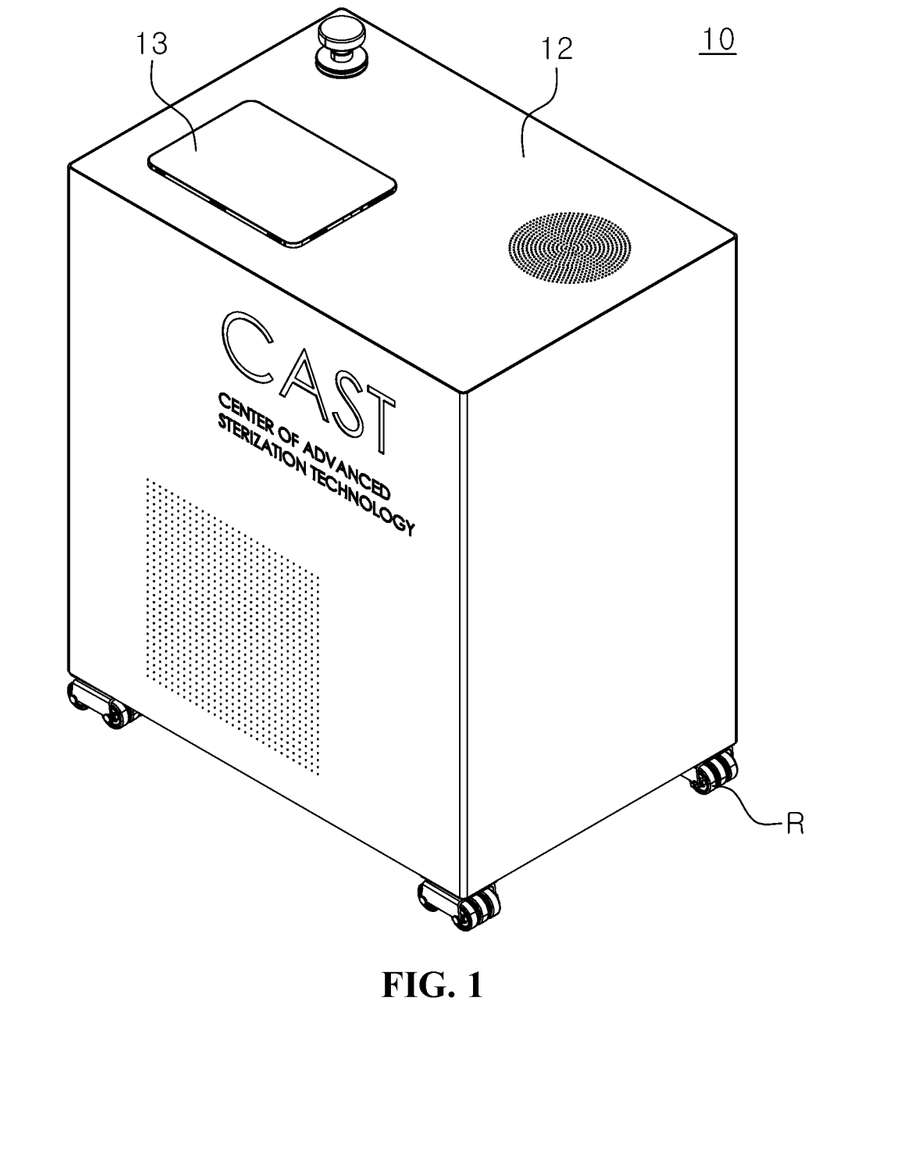
FIGS. 1 to 3 are exemplary views showing the overall appearance of a non-contact microplasma ozonized mist radical sterilizer according to the present invention.
Figure 2:
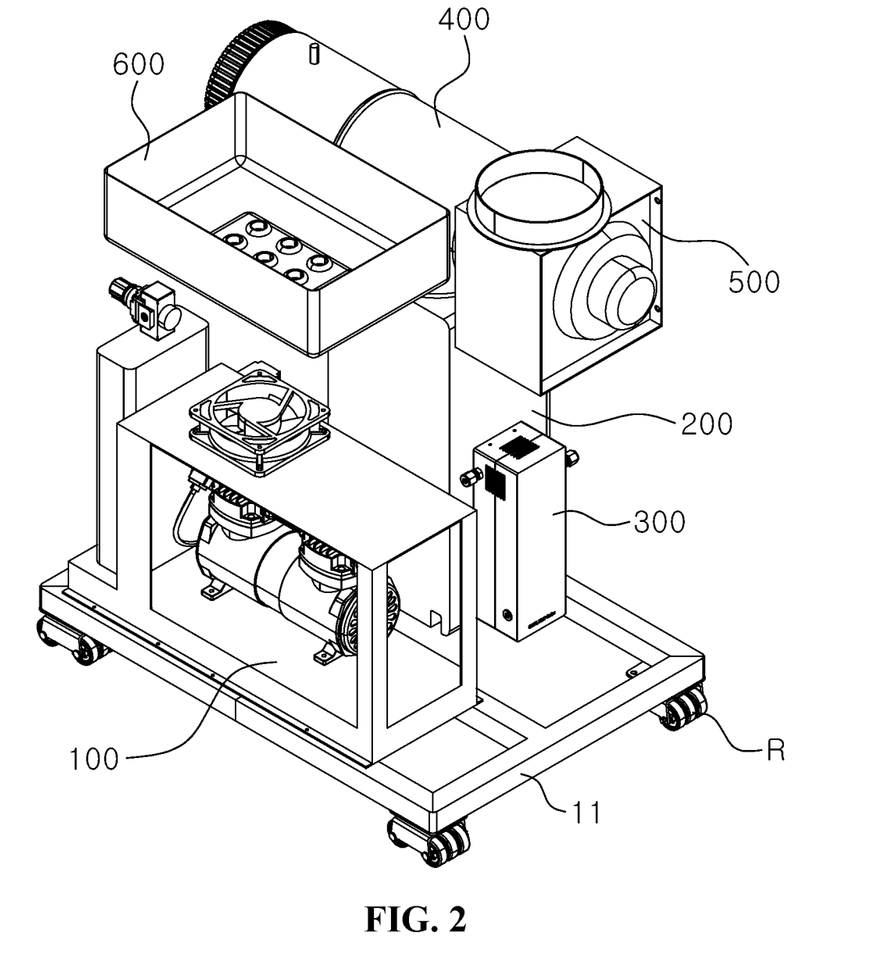
Figure 3:
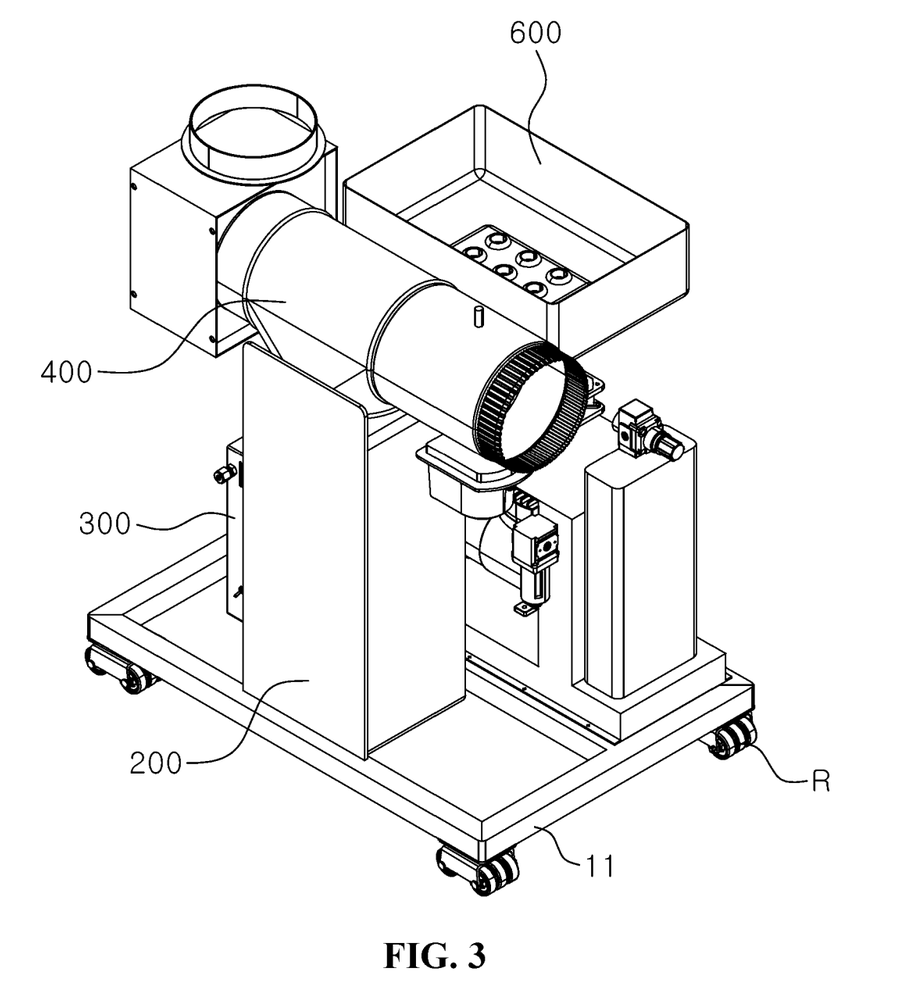

In an aspect, a non-contact microplasma ozonized mist radical sterilizer includes an enclosure 10 having a moving body 11 in a square frame shape in which a plurality of moving wheels R is located on a lower surface, a cover body 12 located on an upper part of the moving member 11, and a display unit 13 provided on an upper surface of the cover body 12, a high-concentration oxygen generator 100 located on the upper surface of the moving body 11 of the enclosure 10, an ozone decomposer 200 provided on the upper surface of the moving body 11 of the enclosure 10 and formed at a position facing the high-concentration oxygen generator 100, a microplasma ozone generator 300 formed at a point on the side of the ozone decomposer 200, an air volume control and selector 400 formed on the ozone decomposer 200, an air circulation pump 500 provided on one side of the air volume control and selector 400 in a longitudinal direction, and a mist generator 600 located at a point perpendicular to the longitudinal direction of the air volume control and selector 400.

Figure 4:
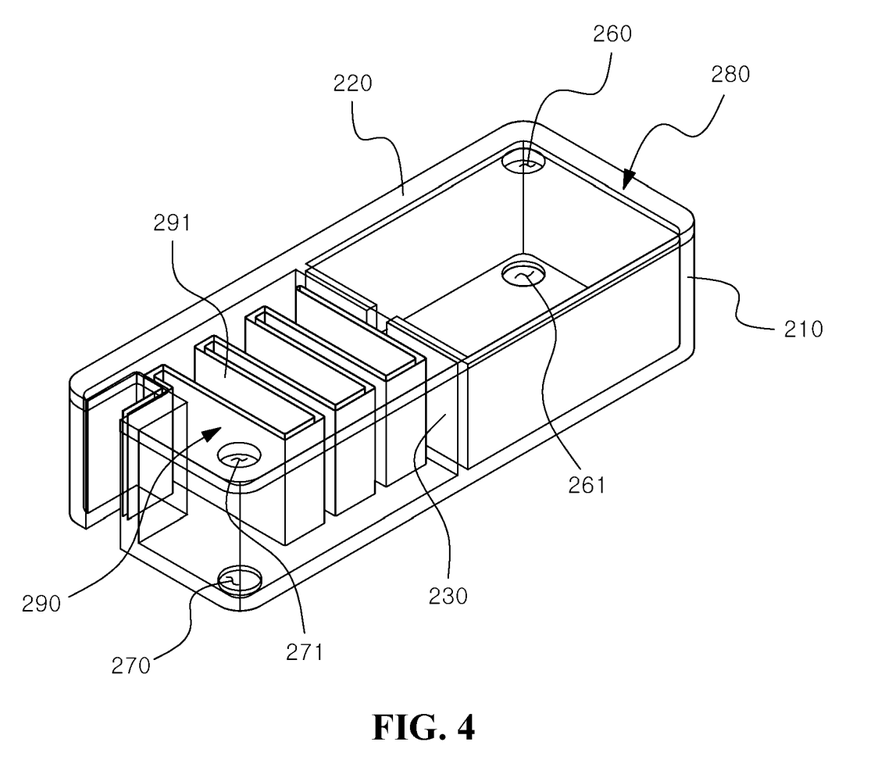
FIGS. 4 and 5 are exemplary views showing a microplasma ozone decomposer of the non-contact microplasma ozonized mist radical sterilizer according to the present invention.
Figure 5:
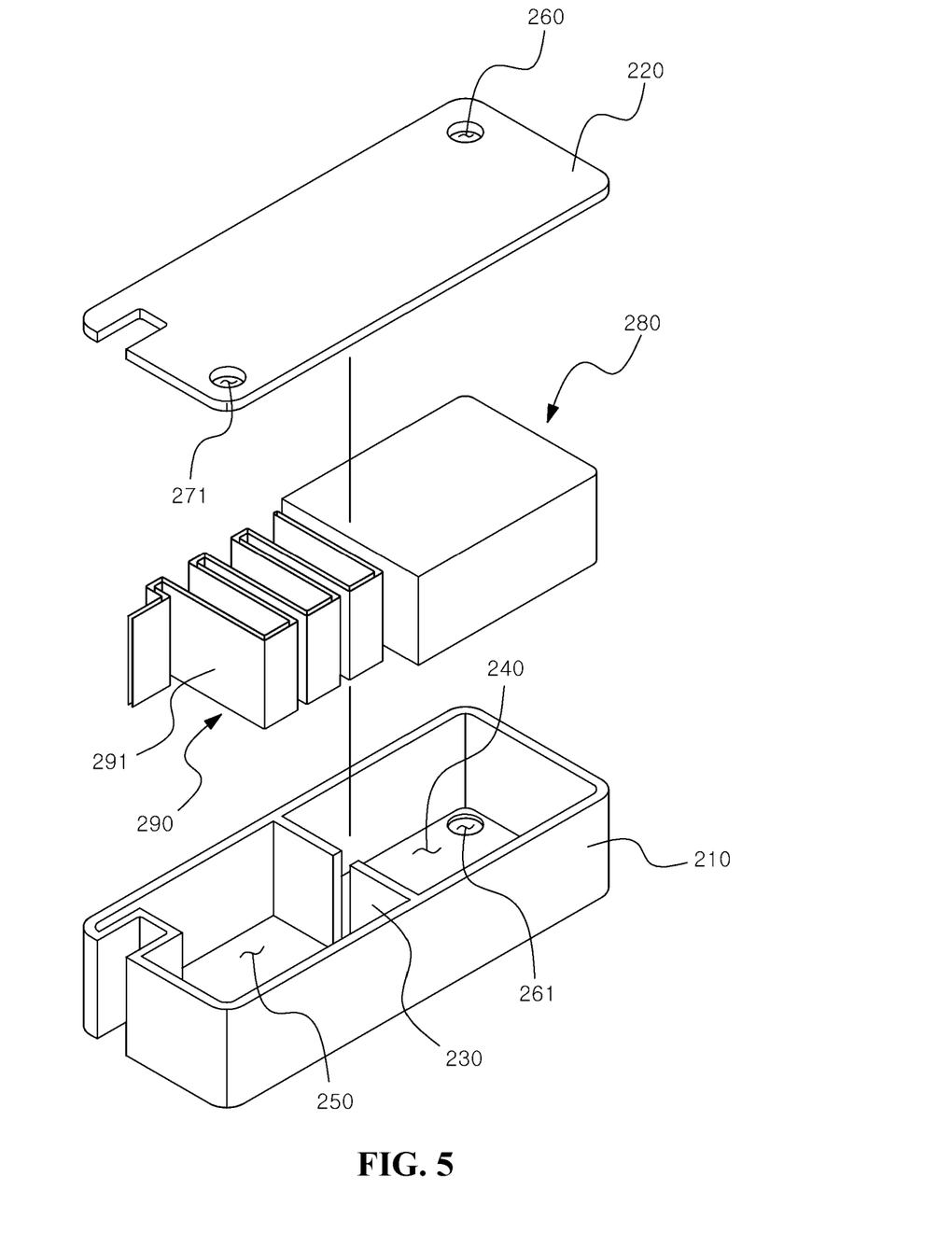

The ozone decomposer 200 has a housing 210 having an internal installation space, an inlet 260 for introducing external gas into the installation space, and an outlet 270 for discharging gas in the installation space to the outside, and
includes a first ozone decomposition unit 280 installed in the installation space of the housing 210 to decompose ozone in external gas flowing into the internal installation space of the housing through the inlet 260, and a second ozone decomposition unit 290 installed in the installation space of the housing 210 to receive gases decomposed by the first ozone decomposition unit 280 and decompose residual ozone in the gases.

Figure 6:
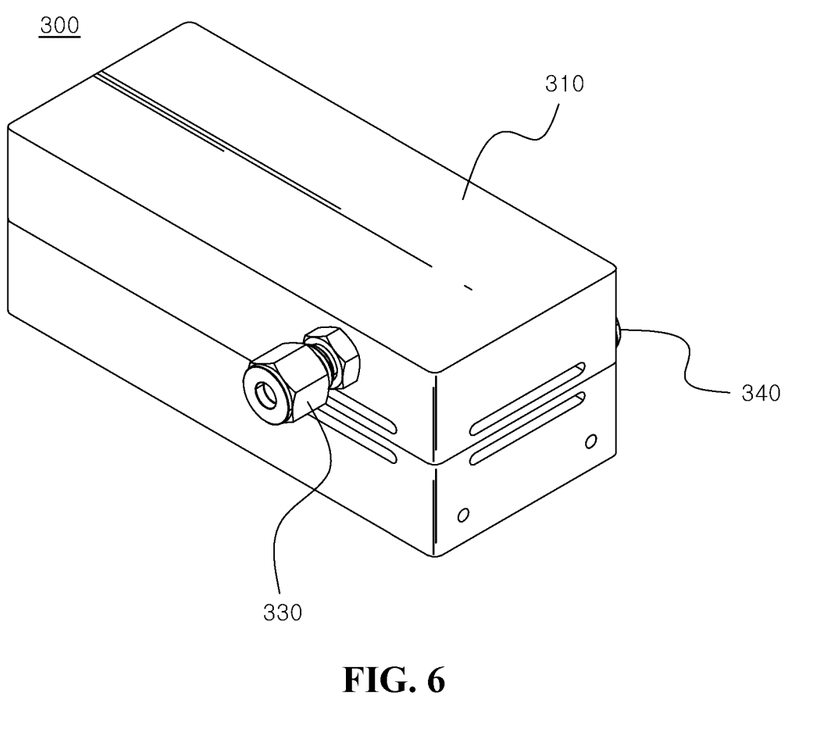
FIGS. 6 and 7 are exemplary views showing a microplasma ozone generator of the non-contact microplasma ozonized mist radical sterilizer according to the present invention.
Figure 7:
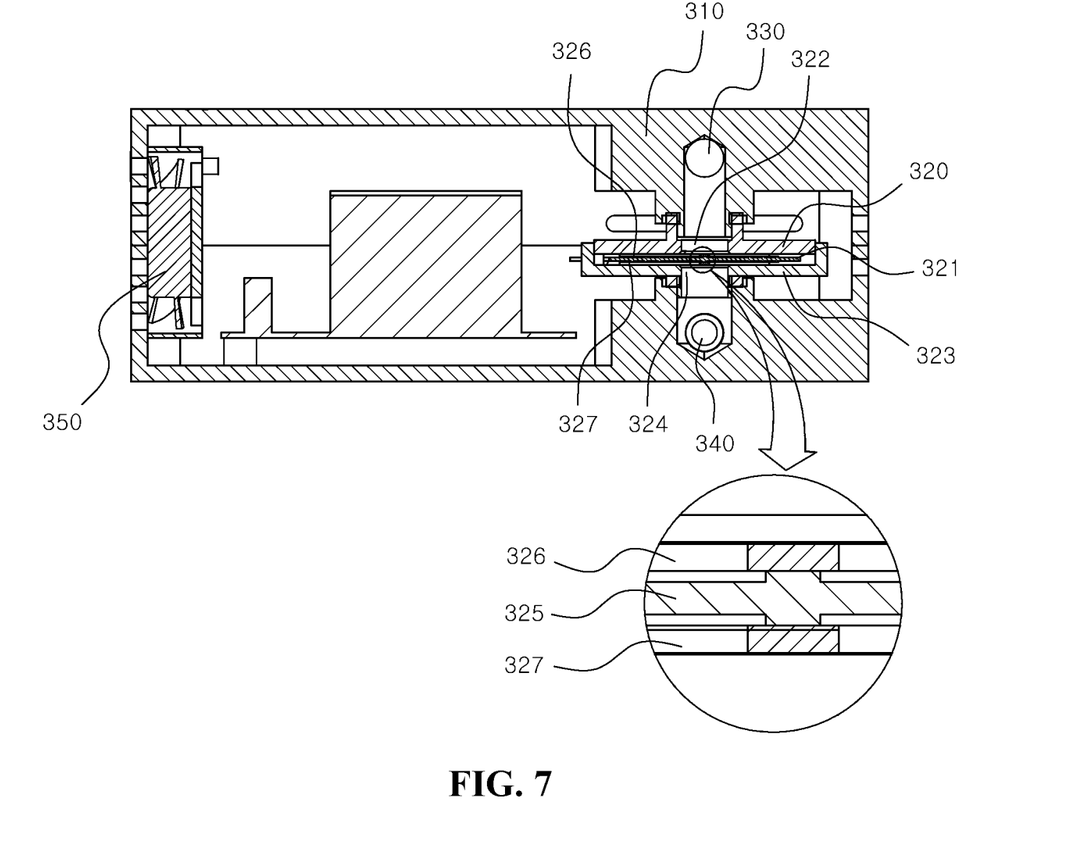

The microplasma ozone generator 300 has a main body 310 having an internal accommodation space, and an ozone generation module 320 installed in the accommodation space inside the main body 310 to generate ozone, an external air supply line 330 is provided to be connected to the ozone generation module 320 from the outside of the main body 310 and supplies air outside the main body to the inside of the ozone generation module, an ozone discharge line 340 is provided to extend from the inside of the ozone generation module 320 to the outside of the main body 310 and discharges ozone generated by the ozone generation module to the outside of the main body, and a cooling fan 350 is provided on one side of the main body 310 to supply air outside the main body to the outer surface of the ozone generation module 320.

Advantageous Effects

The non-contact microplasma ozonized mist radical sterilizer of the present invention generates mist using ozone generated with low-temperature microplasma to perform sterilization using OH radicals generated in water, and is environmentally friendly because it does not use chemical disinfectants.

The heat generating device and the ozone depletion filter are operated to reduce the ozone to oxygen in order to process residual ozone remaining after use for sterilization, and mist is collected to perform final sterilization, and thus stability is improved.

It is possible to improve sterilization by generating sterilized air and mist using ozone generated from microplasma.

DESCRIPTION OF EXEMPLARY EMBODIMENTS

Hereinafter, a non-contact microplasma ozonized mist radical sterilizer according to a preferred embodiment of the present invention will be described with reference to the accompanying drawings.

An enclosure 10 is composed of a moving body 11 in a square frame shape having a plurality of moving wheels R provided on the lower surface thereof, and the moving body is made of metal and is a hollowed border-type frame having four bars bonded in a square or rectangular shape. made of metal and is a hollowed border-type frame having four bars bonded in a square or rectangular shape.

The moving wheels R serve to aid a user in easily moving the non-contact microplasma ozonized mist radical sterilizer of the present invention anywhere.

Here, one lower end of a high-concentration oxygen generator 100 is fixed by further providing one bar at the empty center of the moving body 11, and the other lower end of the high-concentration oxygen generator is fixed to the moving body.

The high-concentration oxygen generator 100 is fixed firmly by bolts.

A cover body 12 includes a plurality of through-holes on the upper and side surfaces thereof to be used for emitting mist or sucking in air.

The cover body 12 is formed on the moving body 11, and a display unit 13 is provided on the upper surface of the cover body 12. The cover body 12 is provided in the shape of a rectangular box with an open lower part to cover the upper surface of the moving body such that a space is provided therein.

All of the high-concentration oxygen generator 100, an ozone decomposer 200, an ozone generator 300, an air volume control and selector 400, an air circulation pump 500, and a mist generator 600 are installed in a space provided between the moving body 11 and the cover body 12.

The display unit 13 displays an operation state of the non-contact microplasma ozonized mist radical sterilizer on a screen such that an operator can identify the operation state at a glance.

As described above, the high-concentration oxygen generator 100 is located on the upper surface of the moving body 11 of the enclosure 10 and is firmly coupled thereto by a fastener such as bolts.

The high-concentration oxygen generator 100 has a frame with one side and the upper surface closed and three surfaces open, an air compressor is installed inside the frame, and a fan is provided on the upper surface of the frame to discharge the heat from the air compressor to the outside.

A housing 210 of the ozone decomposer 200 is a substantially rectangular box-shaped structure with the upper part open, an installation space is formed therein, and a cover 220 for closing the installation space is provided to cover the open upper part. Here, the internal installation space of the housing 210 is partitioned into a first installation space 240 and a second installation space 250 by a partition wall 230 provided inside the housing 210. Here, a part of the partition wall 230 is opened such that the first installation space 240 and the second installation space 250 can communicate with each other.

An inlet 260 for introducing external gas into the internal installation space of the housing 210 is a through-hole having a predetermined diameter and is formed to penetrate the cover 220. The inlet 260 is formed on the cover 220 located above the first installation space 240 such that the outside of the housing 210 and the first installation space 240 communicate with each other.

Further, an outlet 270 for discharging the gas inside the installation space to the outside of the housing 210 is a through-hole having a predetermined diameter and is formed to penetrate the lower part of the housing 210. The outlet 270 is formed at the lower part of the housing 210 where the second installation space 250 is formed to allow the second installation space 250 and the outside of the housing 210 to communicate with each other.

Meanwhile, the present invention further includes an auxiliary outlet 261 formed at the lower part of the housing 210 to communicate with the first installation space 240 and an auxiliary inlet 271 formed at the upper part of the housing 210 to communicate with the second installation space 250.

The auxiliary outlet 261 is a through-hole having a predetermined diameter and is formed to penetrate the lower part of the housing 210. The auxiliary outlet 261 is formed at the lower part of the housing 210 where the first installation space 240 is formed to allow the first installation space 240 and the outside of the housing 210 to communicate with each other.

In addition, the auxiliary inlet 271 is a through-hole having a predetermined diameter and is formed to penetrate the cover 220. The auxiliary inlet 271 is formed at the cover 220 located above the second installation space 250 such that the outside of the housing 210 and the first installation space 240 communicate with each other.

The auxiliary outlet 261 and the auxiliary inlet 271 are components for allowing an upper housing 210 and a lower housing 210 to communicate with each other when a plurality of housings 210 is provided and stacked, and if a single housing 210 is provided, the auxiliary outlet 261 and the auxiliary inlet 271 may be closed with a separate stopper (not shown).

A first ozone decomposition unit 280 is installed in the first installation space 240 to primarily decompose ozone in external gas flowing into the first installation space 240 and includes a support formed of a porous structure and a catalyst supported on the internal pores or the surface of the support. Here, the catalyst may include at least one of manganese dioxide and platinum.

The first ozone decomposition unit 280 reacts with the ozone contained in the gas introduced through the inlet 260 to decompose the ozone into oxygen and oxygen radicals as follows.

$O_3$+catalyst (manganese dioxide, platinum)→$O_2$+O* (oxygen radical)

That is, the ozone contained in the gas introduced through the inlet 250 is decomposed into oxygen by reacting with the catalyst of the first ozone decomposition unit 280.

A second ozone decomposition unit 290 is installed in the second installation space 250 to receive the gases primarily decomposed through the first ozone decomposition unit 280 and secondarily decompose the remaining ozone in the gases, and includes a thermal conductor 291 formed to be bent multiple times and a heat source (not shown) connected to the thermal conductor 291 and supplying heat to the thermal conductor 291.

The heat conductor 291, which is a member formed by bending a metal plate having a predetermined thickness multiple times, is installed inside the first installation space 250 and receives heat from the heat source (not shown) connected to one side thereof to generate heat. The ozone remaining in the gases is decomposed by the heat of the heat conductor 291, and oxygen remaining as a result of decomposition is discharged to the outside of the housing 210 through the outlet 270.

TABLE 1

Ozone half-life by temperature

| Temperature | Half-life |
| --- | --- |
| −50° C. | 3 month |
| −35° C. | 18 days |
| −25° C. | 8 days |
| 20° C. | 3 days |
| 120° C. | 1.5 hours |
| 250° C. | 1.5 seconds |

Table 1 shows the half-life of ozone for each temperature. Ozone is decomposed after about 1.5 hours at 120° C. and after 1.5 seconds at 250° C. The second ozone decomposition unit 290 may adjust the temperature of the thermal conductor 291 depending on the amount of residual ozone or the amount of inflow into the housing 210 and decomposes the ozone into oxygen using the heat of the thermal conductor 291. The amount of residual ozone or the amount of gas flowing into the housing 210 may be detected by a separate sensor. As described above, the ozone in the gas flowing into the housing 210 is primarily decomposed by the first ozone decomposition unit 280 and the residual ozone in the gas decomposed by the first ozone decomposition unit 280 is secondarily decomposed by the second ozone decomposition unit 290, and thus the ozone decomposition time can be reduced, and a larger amount of ozone can be decomposed at the same time.

The microplasma ozone generator 300 has a main body 310 having an accommodation space therein, and an ozone generation module 320 installed in the accommodation space inside the main body 310 to generate ozone.

An external air supply line 330 installed to be connected to the ozone generation module 320 from the outside of the main body 110 and supplying air outside the main body to the inside of the ozone generation module is provided.

An ozone discharge line 340 installed to extend from the inside of the ozone generation module 320 to the outside of the main body 310 and discharging ozone generated by the ozone generation module to the outside of the main body is provided, and a cooling fan 350 installed on one side of the main body 310 to supply air outside the main body to the outer surface of the ozone generation module 320 is provided.

The main body 310 is a structure formed in a rectangular box shape, and an accommodation space is formed therein.

Here, a plurality of cooling slits is provided on one side of the main body 310 such that air outside the main body 310 can be introduced into the accommodation space inside the main body 310.

The ozone generation module 320 includes a first circular floating electrode 321 having an air inlet 322 formed to be connected to the external air supply line 330, a second floating electrode 323 coupled to the first floating electrode 321 and having an ozone discharge port 324 formed to be connected to the ozone discharge line 340, a high-voltage conductor 325 disposed between the first floating electrode 321 and the second floating electrode 323 and generating plasma on a plurality of micro-patterns, a first dielectric 326 disposed between the first floating electrode 321 and the high-voltage conductor 325, and a second dielectric 327 disposed between the high-voltage conductor 325 and the second floating electrode 323.

The first floating electrode 321 is a circular plate having a predetermined thickness, and the air inlet 322 is formed at the center thereof to penetrate the first floating electrode 321.

The second floating electrode 323 is also provided as a circular plate having a predetermined thickness, but is formed to have a larger diameter than the first floating electrode 321. A coupling recess is formed along the outer circumference of the second floating electrode 323 such that the second floating electrode 323 is coupled with the first floating electrode 321 when the first floating electrode 321 is inserted into the coupling groove.

Here, the ozone discharge port 324 is formed at the center of the second floating electrode 323 such that it penetrates the second floating electrode 323.

The high-voltage conductor 325 is a conductor capable of conducting a high voltage, disposed between the first floating electrode 321 and the second floating electrode 323, and a plurality of micro-patterns is formed over the entire area of the high-voltage conductor 325 and plasma can be generated on the micro-patterns.

Here, the thickness of generated micro-plasma may be 50 μm to 300 μm, but is not limited thereto. The shape of the micro-patterns may be at least one of a triangle, an equilateral quadrilateral, a quadrangle, and a semicircle, but is not necessarily limited thereto, and a flat high-voltage conductor 325 without micro-patterns may be provided according to an embodiment. The high-voltage conductor 325 secures a discharge space by adjusting a gap between the high voltage conductors 325 to a size of a micron unit, and an electric field becomes strong near the gap to generate plasma.

In particular, the present invention is designed to be able to adjust the location of plasma generation such that plasma can be generated on a plurality of micro-patterns and has an effect of improving gas discharge efficiency by designing surfaces of various patterns.

The high-voltage conductor 325 has a double-sided electrode structure and thus can increase the amount of discharge more than twice as much as a single-sided electrode structure, and the high-voltage conductor 325 can be disposed in the first floating electrode 321 and the second floating electrode 323 to improve stability.

The first dielectric 326 and the second dielectric 327 are circular plates made of a general dielectric material and are disposed between the first floating electrode 321 and the high-voltage conductor 325 and between the high-voltage conductor 325 and the second floating electrodes 323, respectively.

In the ozone generation module 320 configured as described above, when air is introduced through the air inlet 322 of the first floating electrode 321, the air moves from the center of the upper surface of the high-voltage conductor 325 to the side of the upper surface, and then the air moves from the side of the lower surface of the high-voltage conductor 325 to the center of the lower surface of the high-voltage conductor 325 and is discharged through the ozone discharge port 324 of the second floating electrode 323. At this time, plasma is generated in the micro-patterns of the high-voltage conductor 325 and reacts with the introduced air to generate ozone. The ozone generated as described above is discharged together with the air through the ozone discharge port 324 of the second floating electrode 323.

The air volume control and selector 400 is installed on the ozone decomposer 200.

The air volume control and selector 400 is provided in a pipe shape in which the lower part and both sides are open, and thus is opened in three directions, the open lower part of the air volume control and selector 400 communicates with the ozone decomposer 200, and an air circulation pump 500 is provided in one of the directions in which both sides of the air volume control and selector 400 are opened.

When the air circulation pump 500 sucks in indoor air for 10 minutes, and ozone is generated, mist (low-temperature steam) is discharged through the oxygen generator 100 and the mist generator 600 and thus sterilization is performed.

Thereafter, the air circulation pump 500 sucks in indoor air for 10 minutes, and the ozone decomposer 200 decomposes the residual ozone.

The air circulation pump 500 is a pump for circulating a fluid and serves to circulate and discharge air and ozone in the present invention.

The mist generator 600 is located at a point perpendicular to the longitudinal direction of the air volume control and selector 400.

The mist generator 600 and the high-concentration oxygen generator 100 have a structure in which steam vapor is sucked in according to the flow generated by an air circulation pump (ventilator) and then mixed with air discharged to the outside to be sprayed.

It should be understood that the above-described embodiments are illustrative in all respects and not restrictive, and the scope of the present invention will be indicated by the claims to be described later rather than the detailed description above. In addition, it should be construed that all changes and modifications derived from the meaning and scope of the claims, as well as equivalent concepts, are included in the scope of the present invention.

What is claimed is:

1. A non-contact microplasma ozonized mist radical sterilizer comprising:
    an enclosure having a moving body in a square frame shape in which a plurality of moving wheels is located on a lower surface, a cover body located on an upper part of the moving member, and a display unit provided on an upper surface of the cover body;
    a concentration oxygen generator located on the upper surface of the moving body of the enclosure;
    an ozone decomposer provided on the upper surface of the moving body of the enclosure and formed at a position facing the concentration oxygen generator;
    a microplasma ozone generator formed at a point on the side of the ozone decomposer;
    an air volume control and selector 400 formed on the ozone decomposer;
    an air circulation pump provided on one side of the air volume control and selector in a longitudinal direction; and
    a mist generator located at a point perpendicular to the longitudinal direction of the air volume control and selector,
    wherein the mist generator and the concentration oxygen generator have a structure in which steam vapor is sucked in according to the flow generated by an air circulation pump and then mixed with air discharged to the outside to be sprayed.

2. The non-contact microplasma ozonized mist radical sterilizer according to claim 1, wherein the ozone decomposer has a housing having an internal installation space, an inlet for introducing external gas into the installation space, and an outlet for discharging gas in the installation space to the outside, and includes a first ozone decomposition unit installed in the installation space of the housing to decompose ozone in external gas flowing into the internal installation space of the housing through the inlet, and a second ozone decomposition unit installed in the installation space of the housing to receive gases decomposed by the first ozone decomposition unit and decompose residual ozone in the gases.

3. The non-contact microplasma ozonized mist radical sterilizer according to claim 1, wherein the microplasma ozone generator has a main body having an internal accommodation space, and an ozone generation module installed in the accommodation space inside the main body to generate ozone,
    an external air supply line is provided to be connected to the ozone generation module from the outside of the main body and supplies air outside the main body to the inside of the ozone generation module, and
    an ozone discharge line is provided to extend from the inside of the ozone generation module to the outside of the main body and discharges ozone generated by the ozone generation module to the outside of the main body, and a cooling fan is provided on one side of the main body to supply air outside the main body to the outer surface of the ozone generation module.

* * * * *